US008761444B2

(12) United States Patent
Nakata et al.

(10) Patent No.: US 8,761,444 B2
(45) Date of Patent: Jun. 24, 2014

(54) APPARATUS AND METHOD FOR DETERMINING KIND OF STEEL MATERIAL

(75) Inventors: Takeo Nakata, Osaka (JP); Masami Ikeda, Osaka (JP); Kazuhiro Uchida, Osaka (JP); Makoto Sakamoto, Osaka (JP); Kenji Fujiwara, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 124 days.

(21) Appl. No.: 13/469,447

(22) Filed: May 11, 2012

(65) Prior Publication Data
US 2012/0281876 A1      Nov. 8, 2012

Related U.S. Application Data

(63) Continuation of application No. PCT/JP2010/062760, filed on Jul. 29, 2010.

(30) Foreign Application Priority Data

Nov. 20, 2009   (JP) ................................. 2009-264689

(51) Int. Cl.
    *G06K 9/00*        (2006.01)
(52) U.S. Cl.
    USPC ......................................................... 382/103
(58) Field of Classification Search
    USPC ......................................................... 382/103
    See application file for complete search history.

(56) References Cited

U.S. PATENT DOCUMENTS

| 3,088,308 A | 5/1963 | Danis |
| 8,498,445 B2 * | 7/2013 | Nakata et al. ................. 382/103 |

FOREIGN PATENT DOCUMENTS

| JP | 07-294438 | 11/1995 |
| JP | 07-294439 | 11/1995 |
| JP | 08-086730 | 4/1996 |
| JP | 08-247926 | 9/1996 |
| JP | 3482265 | 12/2003 |
| JP | 2006-090921 | 4/2006 |
| JP | 2008-129003 | 5/2008 |

OTHER PUBLICATIONS

Masaaki et al, JP 07-294438 A (machine translation).*
JIS G 0566: 1980 (English version).*
Japanese Industrial Standard Hagane no Hibana Shiken Hoho, JIS G0566, Japanese Standards Association, Jan. 5, 1980.

* cited by examiner

*Primary Examiner* — Tom Y Lu
(74) *Attorney, Agent, or Firm* — Clark & Brody

(57) ABSTRACT

An apparatus for determining a kind of a steel material includes an image pickup device 11 for imaging a spark, which is produced when the steel material 18 is ground, continuously a plurality of times; a detection device 12 for detecting an alloy spark zone, which corresponds to an alloy spark produced by the grinding of an alloying component contained in the steel material, from each of picked-up images 2 imaged by the image pickup device; a calculation device 13 for calculating the total number of alloy spark zones detected by the detection device; and a judgment device 14 for determining that the steel material consists of a low-alloy steel if the total number is not smaller than a first threshold value, and determining that the steel material consists of a carbon steel if the total number is smaller than the first threshold value.

8 Claims, 9 Drawing Sheets

APPARATUS AND METHOD FOR DETERMINING KIND OF STEEL MATERIAL

TECHNICAL FIELD

The present invention relates to an apparatus and method for determining the kind of a steel material, by which it is judged whether the steel material consists of a carbon steel or a low-alloy steel.

BACKGROUND ART

As a method for determining the carbon content of steel material or for judging whether a steel material consists of a carbon steel or a low-alloy steel, there has been known a method in which an inspector visually observes a spark produced when the steel material is ground by a grinder or the like, and the inspector makes determination or judgment from the state of spark observed. Unfortunately, this method poses a problem that the accuracy of the determination or judgment is unstable, and also a skilled inspector is needed because the determination result or the judgment result depends on the skill of inspector.

A steel material inspection apparatus for making the above-described determination stably and accurately has been proposed (for example, refer to JP3482265B). Unfortunately, the steel material inspection apparatus described in JP3482265B cannot be used to make the above-described judgment stably and accurately. Therefore, it is still desired to develop an apparatus and method capable of making the above-described judgment stably and accurately.

SUMMARY OF INVENTION

An object of the present invention is to provide an apparatus and method for determining the kind of a steel material, by which it can be judged stably and accurately whether the steel material consists of a carbon steel or a low-alloy steel.

The present invention provides an apparatus for determining the kind of a steel material, comprising: an image pickup device for imaging a spark, which is produced when the steel material is ground, continuously a plurality of times; a detection device for detecting an alloy spark zone, which corresponds to an alloy spark produced by the grinding of an alloying component contained in the steel material, from each of picked-up images imaged by the image pickup device; a calculation device for calculating the total number of alloy spark zones by summing up the number of alloy spark zones of each picked-up image detected by the detection device for all of the picked-up images; and a judgment device for determining that the steel material consists of a low-alloy steel if the total number is not smaller than a first threshold value, and determining that the steel material consists of a carbon steel if the total number is smaller than the first threshold value.

As the kinds of sparks produced when the steel material is ground, there are available an alloy spark that is produced only when a steel material containing an alloying component is ground and an ordinary spark that is produced even when either of a steel material not containing an alloying component at all and a steel material containing an alloying component is ground. When the case where a steel material consisting of a carbon steel is ground is compared with the case where a steel material consisting of a low-alloy steel is ground, the number of alloy sparks produced is larger in the case where a steel material consisting of a low-alloy steel is ground. In the apparatus for determining the kind of a steel material in accordance with the present invention, the alloy spark zone, which is a zone displayed by the picked-up image of alloy spark, is detected from the picked-up image of spark produced when the steel material is ground. Regarding the total number of alloy spark zones, the first threshold value for determining whether the steel material consists of a low-alloy steel or a carbon steel is set, and the apparatus for determining the kind of a steel material in accordance with the present invention determines that the steel material consists of a low-alloy steel if the total number of alloy spark zones detected is not smaller than the first threshold value, and determines that the steel material consists of a carbon steel if the total number thereof is smaller than the first threshold value. That is, according to the apparatus for determining the kind of a steel material in accordance with the present invention, based on the magnitude relationship between the first threshold value and the total number of alloy spark zones detected, it is automatically judged whether the steel material consists of a carbon steel or a low-alloy steel. Therefore, according to the apparatus for determining the kind of a steel material in accordance with the present invention, the result of judgment whether the steel material consists of a carbon steel or a low-alloy steel does not depend on the skill of inspector, and the judgment can be made stably. Also, if the total number of alloy spark zones produced when the steel material consisting of a low-alloy steel is ground and the total number of alloy spark zones produced when the steel material consisting of a carbon steel is ground are examined in advance, and the first threshold value is set based on the examination result, the apparatus for determining the kind of a steel material in accordance with the present invention can make the aforementioned judgment accurately.

In the picked-up image obtained by imaging sparks produced when the steel material is ground, there exist the above-described alloy spark zone, an ordinary spark zone that is a zone in which the picked-up image of the above-described ordinary spark is displayed, a periphery zone located at the periphery of each of the alloy spark zone and the ordinary spark zone, and a background zone that is a zone in which the picked-up image on the background of the alloy spark and the ordinary spark is displayed. Hereinafter, the alloy spark zone and the ordinary spark zone are generally referred to as a "spark zone". Each spark zone has a density higher than that of the periphery zone located at the periphery of the spark zone, and the background zone has a density lower than that of any spark zone and any periphery zone. Also, the alloy spark zone and the ordinary spark zone differ from each other in shape. Therefore, as a method for detecting the alloy spark zone from the picked-up image, a method is conceivable in which the spark zone is detected from the picked-up image by binarizing the picked-up image based on density, and the alloy spark zone is detected from the spark zone based on the shape of the detected spark zone.

However, since the brightness of spark differs from spark to spark, in the case where a plurality of spark zones corresponding to a plurality of sparks are present on one sheet of picked-up image, the density differs between spark zones. Also, there is a tendency such that with an increase in the density of a spark zone, the density of the periphery zone located around the spark zone increases. The density of the periphery zone having a high density may become higher than that of the spark zone having a low density. Therefore, if the above-described threshold value for binarization is set at a density lower than the density of the spark zone having a low density, there is a fear that even a pixel constituting the periphery zone having a high density is detected. On the other hand, if the threshold value for binarization is set at a density higher than the density of the periphery zone having a high density, there is a fear that a spark pixel constituting the spark zone having a low density is not detected.

It is preferable that the detection device performs: first processing in which a spark candidate pixel group consisting of pixels which are continuous with each other along a pixel line and have a density not lower than a second threshold value is detected for one pixel line constituting each of the picked-up images; second processing in which the highest density of pixels constituting the spark candidate pixel group is detected, and the pixels constituting each of the spark candidate pixel groups are binarized by a third threshold value which is lower than the highest density and larger than the second threshold value, whereby the pixels constituting a spark pixel group are detected from the pixels constituting each of the spark candidate pixel groups; third processing in which a binarized image representing the spark pixel group is prepared by executing the first processing and the second processing for all of the pixel lines constituting each of the picked-up images, and the spark pixel group continuous on the binarized image is recognized as a spark zone corresponding to a spark produced when the steel material is ground; and fourth processing in which the alloy spark zone is detected from the spark zone recognized by the third processing.

Herein, the pixel line means a row of pixels connected linearly from one end side of picked-up image to the other end side thereof in the transverse or longitudinal direction of the picked-up image, in which the number of pixels in the width direction of row is one.

The spark candidate pixel group means a group of pixels having a possibility of being a spark zone.

The spark pixel group means a group of pixels showing a spark zone.

The second threshold value means a pixel density threshold value that is set to detect the spark candidate pixel group from the picked-up image.

The third threshold value means a pixel density threshold value that is set to detect the pixel constituting the spark pixel group from the pixels constituting the spark candidate pixel group.

The first processing is processing for detecting the spark candidate pixel group consisting of the pixels that are continuous with each other along the pixel line and each have a density not lower than the second threshold value. If the upper limit value that the second threshold value can take is not higher than the density of the spark zone having the lowest density, the spark pixels (the pixels constituting the spark zone) continuous with each other along the pixel line are detected as pixels constituting the spark candidate pixel group. Also, if the lower limit value that the second threshold value can take is higher than the density of the background zone having the highest density, the detection of the pixels constituting the background zone as the pixels constituting the spark candidate pixel group can be excluded. However, as described above, in some cases, the density of the periphery zone having a high density is higher than that of the spark zone having a low density. Therefore, in the case where the second threshold value is set between the above-described upper limit value and the lower limit value, if a periphery zone having a higher density than that of the spark zone exists, the pixels constituting the periphery zone are detected as the pixels constituting the spark candidate pixel group.

The second processing is processing for detecting the highest density of pixels of each of the spark candidate pixel groups and for detecting the pixels constituting the spark pixel group from the pixels constituting each of the spark candidate pixel groups by binarizing the pixels constituting each of the spark candidate pixel groups with the third threshold value that is lower than the highest density and higher than the second threshold value. The spark zone has a higher density than the periphery zone located around the spark zone. Even if the pixels constituting the spark zone and the pixels constituting the periphery zone located around the spark zone are detected as the spark candidate pixel group, by setting the third density threshold value between the density of the pixel constituting the periphery zone and the density of the spark pixel constituting the spark zone, the detection of the pixels constituting the periphery zone as the spark pixels can be excluded. That is, thereby, the spark pixel can be detected accurately from the picked-up image.

Since the second processing is performed for each of the spark candidate pixel groups, the individual third threshold value can be set for each second processing for each of the spark candidate pixel groups. Therefore, even if the density differs between the spark zones constituting each of the spark candidate pixel groups, in the second processing performed on each of the spark candidate pixel groups, the third threshold value can be set in the above-described range, and the pixels constituting the spark zone can be detected from each of the spark candidate pixel groups as the pixels constituting the spark pixel group.

In the third processing, the binarized image representing the spark pixel group is prepared, and in the binarized image, the continuous spark pixel group is recognized as the spark zone. As described above, the spark pixel group is formed by the pixels constituting the spark zone. Therefore, the continuous spark pixel group recognized as the spark zone by the third processing is also formed by the pixels constituting the spark zone. Therefore, the spark zone can be detected exactly by the third processing.

The fourth processing is processing for detecting the alloy spark zone from the spark zone recognized by the third processing. Since the spark zone is detected exactly by the third processing, the alloy spark zone can be detected accurately by the fourth processing.

It is preferable that the fourth processing comprises: determination processing for determining whether or not the spark zone recognized by the third processing falls under a first determination pattern based on the ratio of the width of an end portion on the front side in the spark scatter direction to the width of an end portion on the rear side in the spark scatter direction in the spark zone recognized by the third processing; and detection processing for detecting the spark zone determined to fall under the first determination pattern by the determination processing as the alloy spark zone.

In the alloy spark, the ratio of the width of the end portion on the front side in the alloy spark scatter direction to the width of the end portion on the rear side in the scatter direction is within a predetermined range. The first determination pattern is a pattern for determining whether or not the ratio of the width of the end portion on the front side in the alloy spark scatter direction to the width of the end portion on the rear side in the scatter direction is within the predetermined range. Therefore, according to this preferable configuration, the alloy spark zone can be detected accurately.

It is preferable that the determination processing determines whether or not the spark zone recognized by the third processing falls under the first determination pattern, and also determines whether or not the spark zone recognized by the third processing falls under a second determination pattern based on the relationship between the direction of the spark zone recognized by the third processing and the direction of another rear spark zone which is present at the rear in the scatter direction of the spark zone, and the length of the rear spark zone; and the detection processing detects the spark zone determined to fall under the first and second determination patterns by the determination processing as the alloy spark zone.

At the rear in the scatter direction of the alloy spark, another rear spark scatters. The direction of the rear spark and the direction of the alloy spark have a predetermined relationship, and the length of the rear spark is within a predetermined range. The second determination pattern is a pattern for determining whether or not the direction of the rear spark and the direction of the alloy spark have the predetermined relationship, and whether or not the length of the rear spark is within the predetermined range. Therefore, the spark zone falling under both of the first and second determination patterns has a higher possibility of being the alloy spark zone than the spark zone falling under the first determination pattern only. Therefore, according to this preferable configuration, the alloy spark zone can be detected accurately as compared with the configuration for detecting the spark zone falling under the first determination pattern as the alloy spark zone.

It is preferable that the determination processing determines whether or not the spark zone recognized by the third processing falls under the first and second determination patterns, and also determines whether or not the spark zone recognized by the third processing falls under a third determination pattern based on the distance between the spark zone recognized by the third processing and the rear spark zone; and the detection processing detects the spark zone determined to fall under all of the first to third determination patterns by the determination processing as the alloy spark zone.

The distance between the alloy spark and the rear spark at the rear in the scatter direction of the alloy spark is in a predetermined range. The third determination pattern is a pattern for determining whether or not the distance between the alloy spark and the rear spark at the rear in the scatter direction of the alloy spark is in the predetermined range. Therefore, the spark zone falling under all of the first to third determination patterns has a higher possibility of being the alloy spark zone than the spark zone falling under both of the first and second determination patterns. Therefore, according to this preferable configuration, the alloy spark zone can be detected accurately as compared with the configuration for detecting the spark zone falling under both of the first and second determination patterns as the alloy spark zone.

It is preferable that the determination processing determines whether or not the spark zone recognized by the third processing falls under the first determination pattern, and also determines whether or not the spark zone recognized by the third processing falls under a third determination pattern based on the distance between the spark zone recognized by the third processing and another rear spark zone which is present at the rear in the scatter direction of the spark zone; and the detection processing detects the spark zone determined to fall under the first and third determination patterns by the determination processing as the alloy spark zone.

In this preferable configuration, the spark zone falling under the first and third determination patterns is detected as the alloy spark zone. Therefore, according to this preferable configuration, the alloy spark zone can be detected accurately as compared with the configuration for detecting the spark zone falling under the first determination pattern as the alloy spark zone.

It is preferable that wherein in the case where the steel material consists of a low-alloy steel, the judgment device determines the content of an alloying component in the steel material based on the total number.

The total number of the alloy sparks produced when the steel material consisting of a low-alloy steel is ground increases with an increase in the content of alloying component. Therefore, according to this preferable configuration, the content of alloying component of the steel material consisting of a low-alloy steel can be determined.

And the present invention provides a method for determining the kind of a steel material, comprising: an imaging step of imaging a spark, which is produced when the steel material is ground, continuously a plurality of times; a detecting step of detecting an alloy spark zone corresponding to an alloy spark, which is produced by the grinding of an alloying component contained in the steel material, from each of the picked-up images imaged in the imaging step; a calculating step of calculating the total number of alloy spark zones by summing up the number of alloy spark zones of each picked-up image detected in the detecting step for all of the picked-up images; and a judging step of determining that the steel material consists of a low-alloy steel if the total number is not smaller than a first threshold value, and determining that the steel material consists of a carbon steel if the total number is smaller than the first threshold value.

It is preferable that wherein in the imaging step, a spark produced when the steel material is ground by a grinding member pressed against the steel material with a force not lower than 2.94 N and not higher than 9.8 N is imaged.

If the force with which the grinding member is pressed against the steel material is made not lower than 2.94 N, the number of alloy sparks produced is stabilized. Therefore, according to this preferable method, it can be judged stably whether the steel material consists of a carbon steel or a low-alloy steel. Also, if the pressing force is made not higher than 9.8 N, the steel material can be ground without the occurrence of deep flaws on the steel material. Therefore, according to the above-described preferable method, the aforementioned judgment can be made stably and accurately without the occurrence of deep flaws on the steel material.

The present invention is able to provide an apparatus and method for determining the kind of a steel material, by which it can be judged stably and accurately whether the steel material consists of a carbon steel or a low-alloy steel.

DESCRIPTION OF EMBODIMENTS

Figure 1:
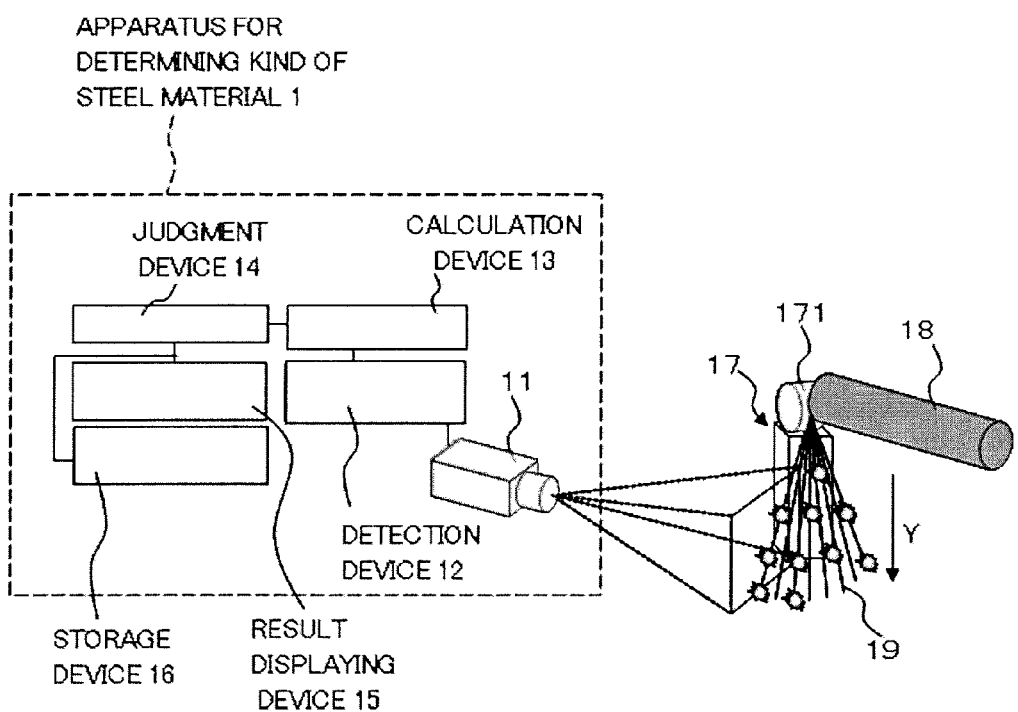
FIG. 1 is a schematic view of the kind determining apparatus of a steel material of this embodiment.

Hereunder, explanation is given of judgment whether a steel material consists of a carbon steel or a low-alloy steel made by using an apparatus for determining the kind of the steel material (hereinafter, referred to a "kind determining apparatus") of this embodiment. FIG. 1 is a schematic view of the kind determining apparatus of this embodiment.

As shown in FIG. 1, the kind determining apparatus 1 includes an image pickup device 11. A grinding member (a grinder 17 in this embodiment) is pressed against a steel material 18, and a spark 19 produced from the steel material 18 by grinding is imaged continuously by the image pickup device 11. At this time, the peripheral face of a disk-shaped grindstone 171 provided in the grinder 17 is pressed against the steel material 18. A force with which the peripheral face of the grindstone 171 is pressed against the steel material 18 is not lower than 2.94 N and not higher than 9.8 N. The circumferential speed of the grindstone 171 of the grinder 17 at the time when the grinder 17 grinds the steel material 18 is 30 m/sec. Also, the exposure time of the image pickup device 11 is 50 msec. The image pickup device 11 continuously images the spark 19 twenty times at time intervals of 50 msec within 1 sec. The steel material 18 contains molybdenum (Mo) as an alloying component. The kinds of the sparks 19 produced when the steel material 18 containing Mo as an alloying component is ground are an alloy spark and an ordinary spark. The alloy spark is a spark that is produced when a steel material containing Mo as an alloying component is ground. The ordinary spark is a spark that is produced when either of a steel material not containing Mo at all as an alloying component and a steel material containing Mo as an alloying component is ground.

Figure 2:
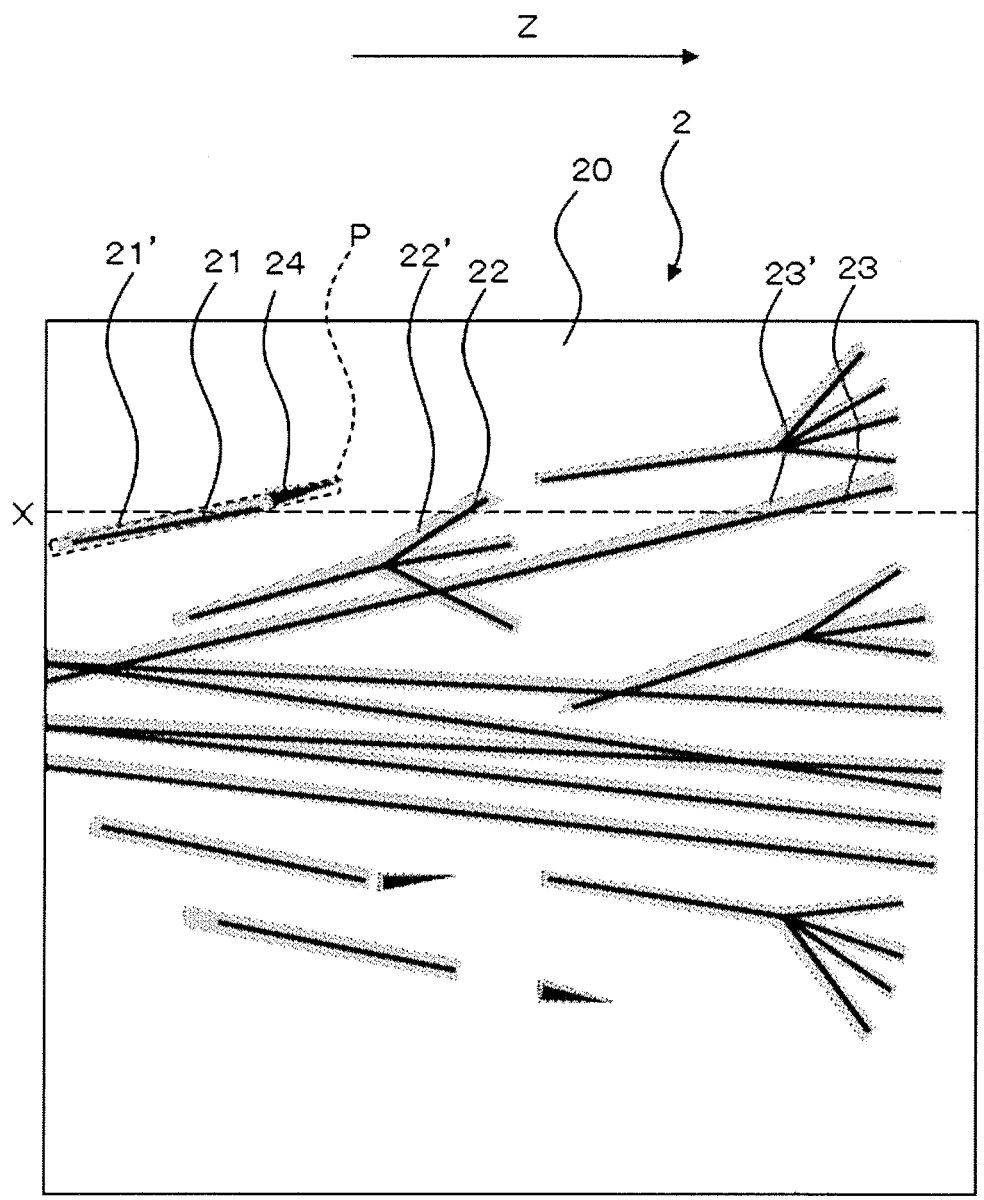
FIG. 2 is a schematic view of a picked-up image picked up by the image pickup device.

FIG. 2 is a schematic view of a picked-up image 2 picked up by the image pickup device 11. The right direction (the direction indicated by the arrow Z) in FIG. 2 corresponds to the direction indicated by the arrow Y in FIG. 1. The direction indicated by the arrow Y is a direction along the tangent line of a portion pressed against the steel material 18 of the portions on the peripheral face of the grindstone 171 and away from that portion. The picked-up image 2 is configured so that M number of pixel lines, each of which is configured by arranging N number of pixels in the right and left direction in FIG. 2, are arranged in the up and down direction in FIG. 2. In the picked-up image 2, there exist an alloy spark zone corresponding to the alloy spark, an ordinary spark zone corresponding to the ordinary spark, a periphery zone located at the periphery of each of the alloy spark zone and the ordinary spark zone, and a background zone that is a zone in which the picked-up image on the background of the alloy spark and the ordinary spark is displayed. In FIG. 2, a spark zone (the general name of the alloy spark zone and the ordinary spark zone) is displayed in black, the periphery zone is displayed in gray, and the background zone is displayed in white. Of the black zone in FIG. 2, the black zone denoted by reference symbol 24 is the alloy spark zone, and any other black zone is the ordinary spark zone.

The image pickup device 11 sends the whole of the picked-up image 2 picked up as described above to a detection device 12.

Upon receipt of the picked-up image 2 from the image pickup device 11, the detection device 12 performs first processing of all of the pixel lines of the whole picked-up image 2. The first processing is performed on each of the pixel lines. In the first processing, a spark candidate pixel group consisting of continuous pixels having a density not lower than a second threshold value is detected from the pixel lines to be subjected to the first processing.

Figure 3:
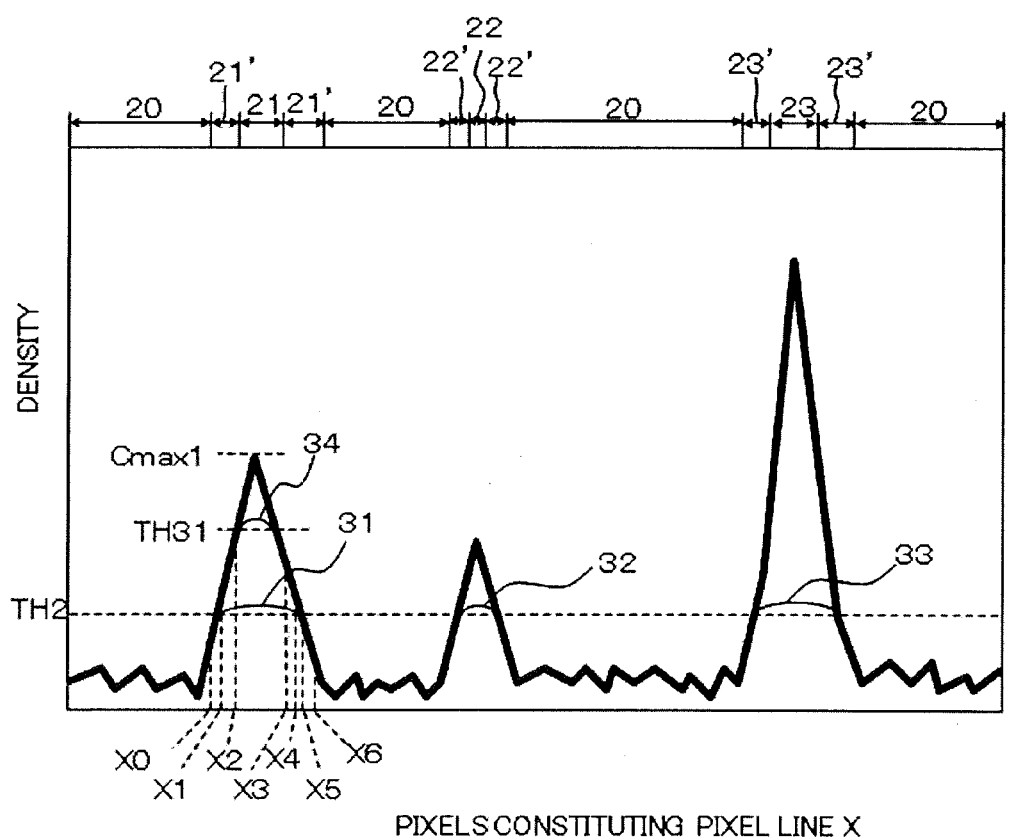
FIG. 3 is a graph showing the density distribution of the pixel line X.

Hereunder, the first processing performed on a pixel line X (refer to FIG. 2) is explained. FIG. 3 is a graph showing the density distribution of the pixel line X (refer to FIG. 2). As shown in FIG. 2, on the pixel line X, there exist spark zones 21, 22 and 23 and periphery zones 21', 22' and 23' located at the periphery of the spark zones 21, 22 and 23, respectively.

As shown in FIG. 3, each of the spark zones 21, 22 and 23 has a higher density than each of the periphery zones 21', 22' and 23' located at the periphery of each of the spark zones 21, 22 and 23. Also, a background zone 20 has a lower density than any of the spark zones 21, 22 and 23 and any of the periphery zones 21', 22' and 23'. The densities of the spark zones 21, 22 and 23 differ from each other. Also, the density in the periphery zones 21', 22' and 23' is higher at a position closer to the spark zones 21, 22 and 23.

As shown in FIG. 3, the pixels located between a pixel X0 and a pixel X2 existing on the right-hand side of the pixel X0 in the figure and the pixels located between a pixel X3 existing on the right-hand side of the pixel X2 in the figure and a pixel X6 existing on the right-hand side of the pixel X3 in the figure constitute the periphery zone 21'. Also, the pixels located between the pixel X2 and the pixel X3 (not including the pixel X2 and the pixel X3) constitute the spark zone 21.

At the time of the above-described first processing, the detection device 12 first determines whether or not the density of each of the pixels constituting the pixel line X is not lower than the second threshold value TH2 in the order from a pixel close to the end portion on one side (in this embodiment, the left-hand side in FIG. 3) of the pixel line X to the other side. This second threshold value TH2 is a density not higher than the lowest value of the densities that the pixels constituting any spark zone existing in the picked-up image 2 have, and is a density higher than the highest value of the densities that the pixels constituting the background zone have. As a method for setting the second threshold value TH2 at a value in the above-described range, there can be cited, for example, a method in which the density slightly exceeding the highest density of the densities that the pixels constituting the picked-up image 2 picked up by the image pickup device 11 when no spark is produced have is set at the second threshold value TH2.

As shown in FIG. 3, of the pixels that constitute the pixel line X and have a density not lower than the second threshold value TH2, the pixel closest to the end portion on one side of the pixel line X is a pixel X1 located between the pixel X0 and the pixel X2. Therefore, the detection device 12 first detects the pixel X1 as a pixel having a density not lower than the second threshold value TH2. The detection device 12 recognizes the first detected pixel X1 as a start point pixel that is a pixel at which the detection of spark candidate pixel group is started.

After the pixel X1 has been recognized as the start point pixel, the detection device 12 determines whether or not the density of each of the pixels existing on the other side of the start point pixel X1 on the pixel line X is lower than the second threshold value TH2 in the order from a pixel close to the start point pixel X1. As shown in FIG. 3, among the pixels existing on the other side of the start point pixel X1 on the pixel line X, of the pixels having a density lower than the second threshold value TH2, the pixel closest to the start point pixel X1 is a pixel X5 located between the pixel X3 and the pixel X6.

Therefore, the detection device 12 first detects the pixel X5 as a pixel having a density lower than the second threshold value TH2. The detection device 12 recognizes a pixel X4 adjacent to the detected pixel X5 on one side of the pixel X5 on the pixel line X as an end point pixel that is a pixel at which the detection of spark candidate pixel group is finished. The detection device 12 detects a pixel group formed by the pixels existing between the start point pixel X1 and the end point pixel X4 as a spark candidate pixel group 31 (refer to FIG. 3).

If the second threshold value TH2 is set in the above-described range, the density of the pixels constituting the background zone 20 becomes lower than the second threshold value TH2, the detection of the pixels constituting the background zone 20 as pixels constituting the spark candidate pixel group 31 can be excluded, and the pixels constituting the spark zones 21, 22 and 23 are detected as pixels constituting the spark candidate pixel group.

After detecting the spark candidate pixel group 31, the detection device 12 recognizes start point pixels and end point pixels and detects other spark candidate pixel groups from among the pixels existing on the other side of the end point pixel X4 on the pixel line X. In this embodiment, the detection device 12 detects a spark candidate pixel group 32 formed by the pixels constituting the spark zone 22 and the pixels constituting the periphery zone 22' and a spark candidate pixel group 33 formed by the pixels constituting the spark zone 23 and the pixels constituting the periphery zone 23'.

After finishing the first processing of all of the pixel lines of the whole picked-up image 2, the detection device 12 performs second processing of all of the spark candidate pixel groups. The second processing is performed on each of the spark candidate pixel groups. In the second processing, the pixels constituting a spark pixel group are detected from the pixels constituting each of the spark candidate pixel groups.

Hereunder, the second processing performed on the spark candidate pixel group 31 is explained. As shown in FIG. 3, the detection device 12 binarizes the pixels constituting the spark candidate pixel group 31 by means of a third threshold value TH31 that is lower than the highest density Cmax1 of the pixels constituting the spark candidate pixel group 31 and exceeds the second threshold value TH2. The detection device 12 detects the pixels having a density not lower than the third threshold value TH31 as pixels constituting a spark pixel group 34. In this embodiment, the third threshold value TH31 is set at a density higher than the highest value of the densities that the pixels constituting the periphery zone 21' have, and is not higher than the lowest value of the densities that the pixels constituting the spark zone 21 have. Therefore, all of the pixels constituting the spark zone 21 are detected as pixels constituting the spark pixel group 34, and the pixels constituting the periphery zone 21' are not detected as pixels constituting the spark pixel group 34. The spark pixel group 34 is formed by the pixels constituting the spark zone 21.

Since the second processing is performed on each of the spark candidate pixel groups, individual third threshold values can be set for each second processing performed on each of the spark candidate pixel groups. Therefore, even if the density of spark zone constituting each of the spark candidate pixel groups differs, in the second processing performed on each of the spark candidate pixel groups, the third threshold value can be set between the spark zone and the periphery zone, and the pixels constituting the spark zone can be detected from each of the spark candidate pixel groups.

Figure 4:
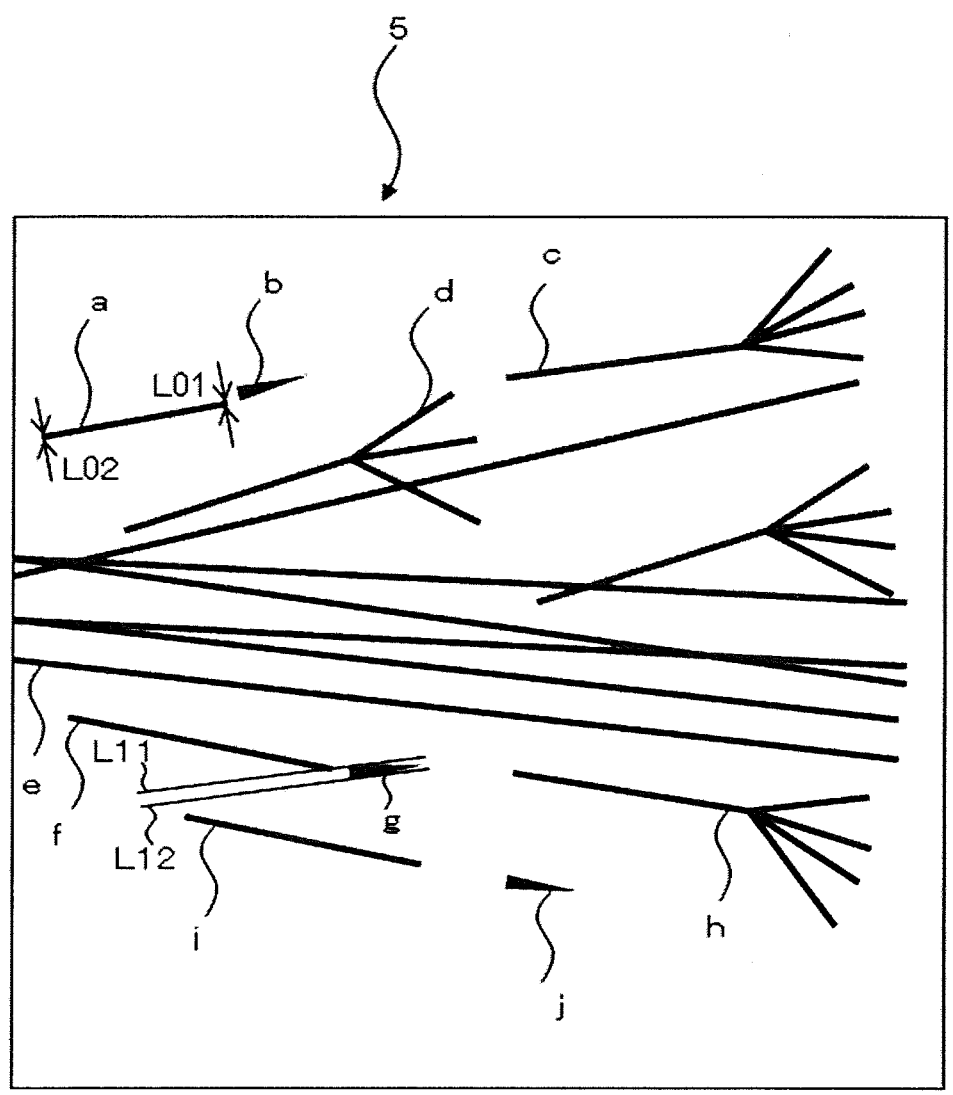
FIG. 4 is a binarized image of the picked-up image

After finishing the second processing, the detection device 12 performs third processing. In the third processing, first, a binarized image of the picked-up image 2 is prepared from the picked-up image 2. The binarized image of the picked-up image 2 is an image in which of the pixels constituting the picked-up image 2, which are sent from the image pickup device 11, the pixels detected as pixels constituting the spark pixel group in the second processing and other pixels are binarized into black color and white color. FIG. 4 shows a binarized image 5 of the picked-up image 2 shown in FIG. 2. In FIG. 4, the pixels detected as pixels constituting the spark pixel group is displayed in black, and the pixels not detected as pixels constituting the spark pixel group is displayed in white.

After preparing the binarized image 5 of the picked-up image 2, in the binarized image 5 of the picked-up image 2, the detection device 12 recognizes the spark pixel groups continuous with each other as spark zones a to j corresponding to the spark produced when the steel material 18 is ground. To recognize the spark zones a to j, the binarized image 5 is labeled, a cluster of spark pixel groups is detected, and the detected cluster is recognized as one spark zone. As described above, the spark pixel group is formed by the pixels constituting the spark zone. Therefore, the cluster in which the spark pixel groups are continuous, which is recognized as the spark zone by the third processing is also formed by the pixels constituting the spark zone. For this reason, the spark zone is detected exactly by the third processing.

After finishing the third processing, the detection device 12 performs fourth processing on all of the spark zones recognized by the third processing. The fourth processing is performed for each of the spark zones recognized by the third processing. Hereunder, the fourth processing performed on the spark zones a to j (refer to FIG. 4) recognized by the third processing is explained.

The detection device 12 first calculates the number of pixels constituting each of the spark zones a to j. The detection device 12 extracts spark zones, in which the number of pixels is smaller than a predetermined number (for example, smaller than 125 pixels), from among the spark zones a to j. As shown in FIG. 4, the spark zones c, d, e and h each have a large area, and are formed by the number of pixels not smaller than the predetermined number. Herein, therefore, it is assumed that the spark zones a, b, f, g, i and j were extracted.

Next, the detection device 12 extracts spark zones, the length of which is smaller than a predetermined value, from among the extracted spark zones. The length of spark zone can be defined as a distance between a pixel that is present on the leftmost side in the figure and a pixel that is present on the rightmost side in the figure of the pixels constituting the spark zone. As shown in FIG. 4, the spark zones f and i are long, and herein, it is assumed that the spark zones a, b, g and j were extracted.

Next, the detection device 12 calculates the width of an end portion on the front side (hereinafter, referred to as a "front end portion") in the spark scatter direction in the spark zone extracted (having a length smaller than the predetermined value) and the width of an end portion on the rear side (hereinafter, referred to as a "rear end portion") in the scatter direction, and determines whether or not the spark zone fall under a first determination pattern. In the binarized image 5 of FIG. 4, the front side in the spark scatter direction is the right-hand side, and the rear side in the spark scatter direction is the left-hand side. Also, the front end portion is, for example, a portion formed by pixels that are present on the right-hand side in the binarized image 5 of the pixels constituting the spark zone. The rear end portion is, for example, a portion formed by pixels that are present on the left-hand side in the binarized image 5 of the pixels constituting the spark zone. Also, the widths of the front end portion and the rear end portion are, for example, dimensions of the front end portion and the rear end portion in the direction perpendicular to a straight line passing through the central portion of the front end portion and the central portion of the rear end portion. Explaining by taking the spark zone a as an example, the detection device 12 determines whether or not the spark zone a falls under the first determination pattern based on the ratio of the width L01 of the front end portion to the width L02 of the rear end portion. In this embodiment, in the case where the ratio of the width L01 of the front end portion to the width L02 of the rear end portion is not higher than a predetermined value defined beforehand (for example, 0.4), the detection device 12 determines that the spark zone a falls under the first determination pattern. As shown in FIG. 4, since the spark zone a has no difference in width between the front end portion and the rear end portion, it is determined that the spark zone a does not fall under the first determination pattern. It is assumed that the detection device 12 determined that only the spark zones b, g and j fall under the first determination pattern.

As described above, the alloy spark produced when a steel material containing Mo as an alloying component is ground has a spear-like shape. The spear-like shape means a shape such that the rear end portion located on the rear side in the spark scatter direction has a greater width than the front end portion located on the front side in the spark scatter direction. Therefore, the spark zone determined to fall under the first determination pattern has a high possibility of being an alloy spark zone.

The alloy spark is small in size and short in length. Therefore, the spark zone having a large number of pixels or the spark zone being long in length has a low possibility of being an alloy spark zone. As described above, by determining whether the first determination pattern applies to only the spark zone that is formed by the number of pixels smaller than the predetermined number and has a length smaller than the predetermined value, a spark zone having a high possibility of being an alloy spark zone can be detected rapidly with a small amount of calculation.

Figure 5:
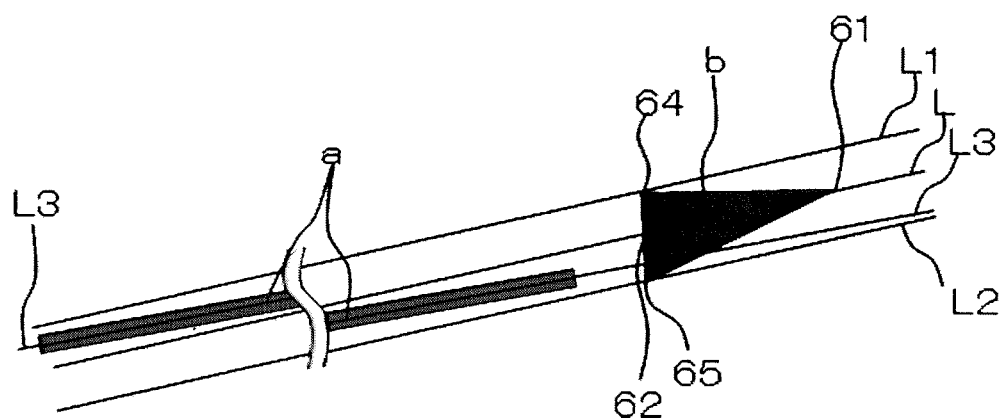
FIG. 5 is an enlarged view showing the vicinity of the spark zone a and the spark zone b in the binarized image in FIG. 4.

The detection device 12 determines whether or not the spark zone having been determined to fall under the first determination pattern also falls under a second determination pattern. Hereunder, this determination made for the spark zone b is explained. First, in the binarized image 5, it is determined whether or not any other spark zone having a predetermined length is present on the left-hand side (on the rear side in the spark scatter direction) of the spark zone b. FIG. 5 is an enlarged view showing the vicinity of the spark zone a and the spark zone b in the binarized image 5 in FIG. 4. Herein, the left-hand side of the spark zone b means a zone that is on the left-hand side of the spark zone b and is held between a first section line L1 and a second section line L2. The first section line L1 is a straight line that is parallel to a straight line L passing through a central portion 61 in the width direction of the front end portion of the spark zone b and a central portion 62 in the width direction of the rear end portion thereof, and passes through a portion 64 of the spark zone b, which is most distant from the straight line L on one direction side in the direction perpendicular to the straight line L. The second section line L2 is a straight line that is parallel to the straight line L, and passes through a portion 65 of the spark zone b, which is most distant from the straight line L on the other direction side in the direction perpendicular to the straight line L. Also, the phrase "present on the left-hand side of the spark zone b" means that the whole of spark zone falls in a zone that is held between the first section line L1 and the second section line L2 and on the left-hand side of the spark zone b. As shown in FIG. 5, the whole of the spark zone a falls in the left-hand side zone that is on the left-hand side of the spark zone b and held between the first section line L1 and the second section line L2. Also, the spark zone a has a predetermined length (a length corresponding to the length of spark scattering so as to follow the alloy spark at the rear in the alloy spark scatter direction). Therefore, the detection device 12 determines that another spark zone a having the predetermined length is present on the left-hand side of the spark zone b.

After determining that another spark zone a having the predetermined length is present on the left-hand side of the spark zone b, the detection device 12 determines, based on the relationship between the direction of the spark zone b and the direction of the spark zone a, whether or not the spark zone b also falls under the second determination pattern. The direction of the spark zone b is the direction of the aforementioned straight line L. The direction of the spark zone a is, for example, the direction of a straight line L3 passing through a pixel that is present on the leftmost side and a pixel that is present on the rightmost side of the pixels constituting the spark zone a.

As one specific example of the relationship between the direction of the spark zone b and the direction of the spark zone a, an angle formed between the direction of the spark zone b and the direction of the spark zone a can be cited. In this case, when the formed angle is not larger than a predetermined angle, the detection device 12 determines that the spark zone b also falls under the second determination pattern.

In this example, the angle formed between the direction of the spark zone b and the direction of the spark zone a is not larger than the predetermined angle, and therefore the detection device 12 determines that the spark zone b also falls under the second determination pattern.

As another specific example of the relationship between the direction of the spark zone b and the direction of the spark zone a, the ratio of an angle $\theta'$ formed between the direction of the spark zone b and the direction of the spark zone a to an angle $\theta$ formed between the direction of the spark zone b and a predetermined direction can be cited. In this case, when the ratio is not higher than a predetermined value (for example, not higher than 0.3), the detection device 12 determines that the spark zone b also falls under the second determination pattern. The predetermined direction is, for example, the right direction in the binarized image 5, that is, a direction along the tangent line of a portion pressed against the steel material 18 of the portions on the peripheral face of the grindstone 171 and away from that portion.

At the rear in the alloy spark scatter direction, another rear spark scatters so as to follow the alloy spark. The angle formed between the direction of this rear spark and the direction of the alloy spark is within a predetermined range, and the length of the rear spark is within a predetermined range. Therefore, the spark zone determined to fall under the second determination pattern has a higher possibility of being an alloy spark zone than the spark zone determined to fall under the first determination pattern only. Herein, it is assumed that the detection device 12 determined that the spark zone j, like the spark zone b, falls under the second determination pattern. On the other hand, it is assumed that the detection device 12 determined that the spark zone g does not fall under the second determination pattern because the whole of the rear spark zone f is on the left-hand side of the spark zone g, but does not fall in the left-hand side zone held between a first section line L11 and a second section line L12.

Figure 6:
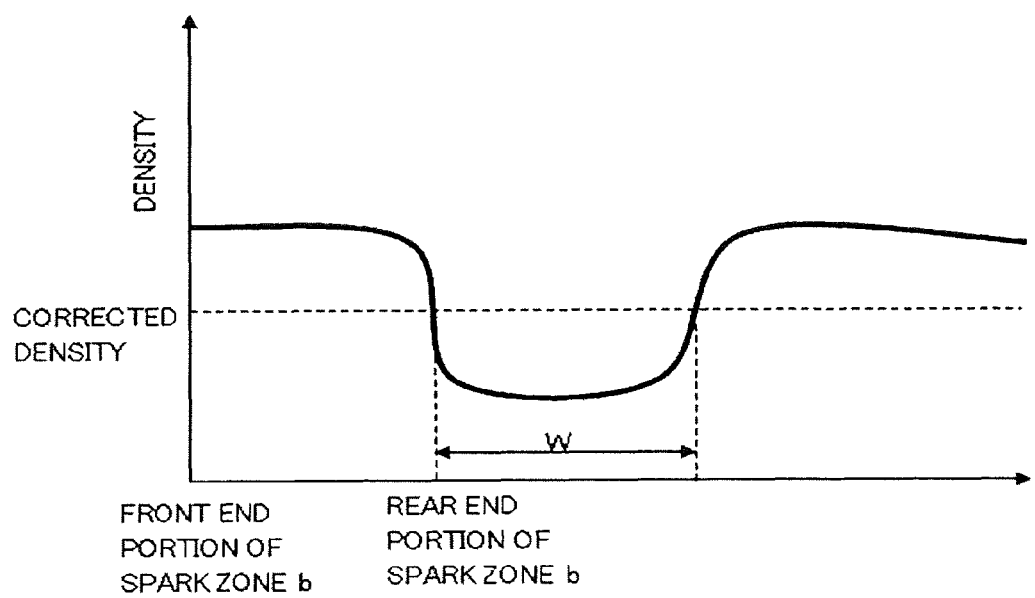
FIG. 6 is a graph showing the density distribution in the longitudinal direction of the corresponding zone.

The detection device 12 determines whether or not the spark zone having been determined to fall under the second determination pattern also falls under a third determination pattern. Hereunder, this determination made for the spark zone b is explained. First, the detection device 12 recognizes, from the picked-up image 2 shown in FIG. 2, a corresponding zone P (refer to FIG. 2) that is held between the first section line L1 and the second section line L2 shown in FIG. 5 and corresponds to a straight line shaped zone extending a predetermined distance from the front end portion of the spark zone b to the rear in the spark scatter direction. This straight line shaped zone extends at least to the rear in the scatter direction beyond the rear end portion of the spark zone b. The detection device 12 calculates the density distribution of the corresponding zone P in the longitudinal direction of the corresponding zone P (the direction corresponding to the direction parallel to the first section line L1 and the second section line L2). FIG. 6 shows the density distribution. The detection device 12 calculates an average density in the longitudinal direction of the corresponding zone P from this density distribution. The detection device 12 calculates a corrected density obtained by adding or subtracting a predetermined amount of density to or from the calculated average density. The detection device 12 recognizes a portion corresponding to the rear end portion of the spark zone b from the corresponding zone P. The detection device 12 determines that in the case where, at the rear of the recognized portion corresponding to the rear end portion, the length W of a section in which the density is lower than the corrected density is within a predetermined range, the spark zone b also falls under the third determination pattern. If the length W of the section in which the density is lower than the corrected density is not within the predetermined range, it is determined that the spark zone b does not fall under the third determination pattern.

The aforementioned rear spark scatters so as to be slightly separate from the alloy spark to the rear in the alloy spark scatter direction. Therefore, at the rear in the spark scatter direction of the alloy spark zone, a section in which the density is low by a distance corresponding to the slight distance exists. Therefore, the spark zone determined to also fall under the third determination pattern has a higher possibility of being an alloy spark zone than the spark zone determined to fall under the first and second determination patterns only.

In this example, as shown in FIG. 2, at the rear in the spark scatter direction of the spark zone b, the spark zone a is present so as to be separated slightly. Therefore, herein, it is assumed that the detection device 12 determined that the spark zone b falls under the third determination pattern. On the other hand, as shown in FIG. 4, the spark zone j and the spark zone i are separated greatly from each other. Therefore, herein, it is assumed that the detection device 12 determined that the spark zone j does not fall under the third determination pattern.

As described above, the detection device 12 detects the spark zone b (the spark zone corresponding to the spark zone 24 in FIG. 2) determined to fall under all of the first to third determination pattern, of the spark zones a to j as an alloy spark zone.

A calculation device 13 calculates the total number of alloy spark zones by summing up the number of alloy spark zones of each picked-up image detected by the detection device 12 as described above for all of the picked-up images.

In the case where the total number of spark zones calculated by the calculation device 13 is not smaller than a first threshold value, a judgment device 14 determines that the steel material 18 is a steel material consisting of a low-alloy steel, and in the case where the total number is smaller than the first threshold value, a judgment device 14 determines that the steel material 18 is a steel material consisting of a carbon steel. The low-alloy steel means a steel containing less than 2% of Cr of the steels that meet at least one of the following conditions 1 to 4:

Condition 1: The Cr content is 0.5% or more.
Condition 2: The Ni content is 0.5% or more.
Condition 3: The Mo content is 0.25% or more.
Condition 4: The Cu content is 0.25% or more.

Also, the carbon steel means a steel that does not meet all of the above conditions 1 to 4.

Figure 7:
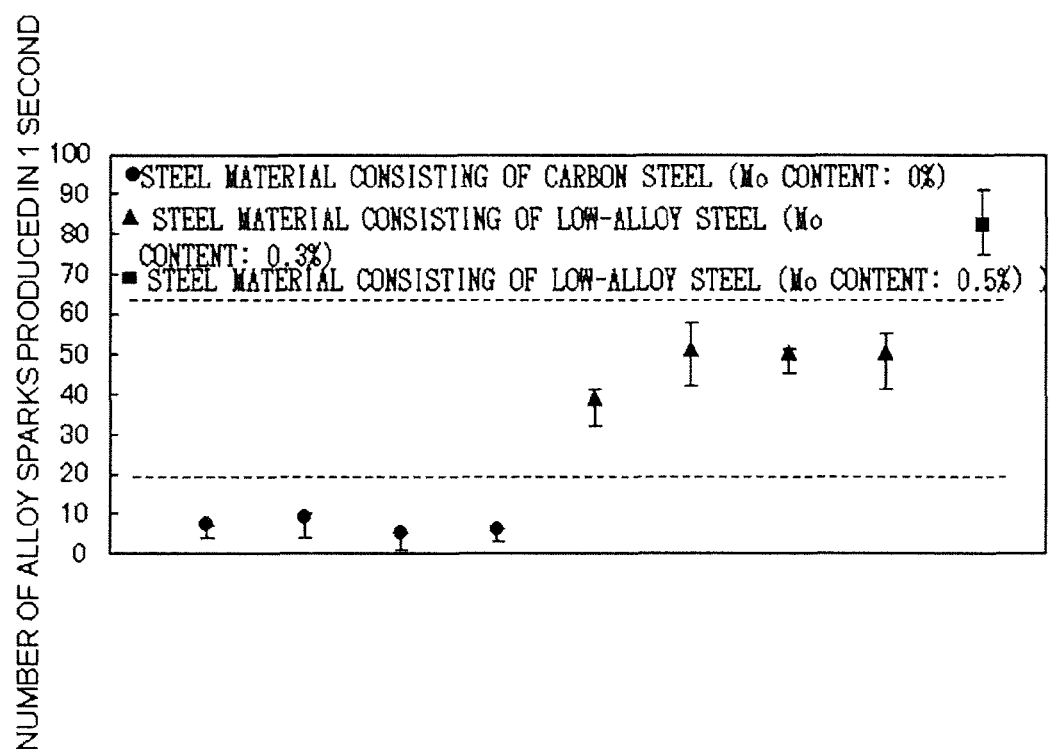
FIG. 7 is a graph showing the total number of alloy spark zones produced in the case where the steel material consisting of a low-alloy steel is ground and the total number of alloy spark zones produced in the case where the steel material consisting of a carbon steel is ground.

FIG. 7 is a graph showing the total number of alloy spark zones calculated by the calculation device 13 for four samples of steel material consisting of a carbon steel and total number of alloy spark zones calculated by the calculation device 13 for five samples of steel materials consisting of a low-alloy steel. As shown in FIG. 7, comparing the case where the steel material consisting of a carbon steel is ground with the case where the steel material consisting of a low-alloy steel is ground, the number of alloy spark zones (alloy sparks) is larger in the latter case. Therefore, if the first threshold value is set at a number between the total number of alloy spark zones produced in the case where the steel material consisting of a low-alloy steel is ground and the total number of alloy spark zones produced in the case where the steel material consisting of a carbon steel is ground, the kind determining apparatus 1 can judge whether a steel material consists of a carbon steel or a low-alloy steel. Therefore, according to the kind determining apparatus 1, the judgment can be made stably so that the judgment result does not depend on the skill of inspector.

Also, in the case where it is determined that the steel material 18 is a steel material consisting of a low-alloy steel, the judgment device 14 determines the contents of alloying components in the steel material 18 based on the total number of alloy spark zones calculated by the calculation device 13. As shown in FIG. 7, the total number of alloy sparks produced when the steel material consisting of a low-alloy steel is ground increases with an increase in Mo content. Therefore, in the case where the steel material 18 is a steel material consisting of a low-alloy steel, the kind determining apparatus 1 can determine the content of alloying component in the steel material consisting of a low-alloy steel. Specifically, the correlation between the content of alloying component in the steel material consisting of a carbon steel and a low-alloy steel and the total number of alloy sparks is examined in advance by using a plurality of samples, and a correlation equation for calculating the content of alloying component from the total number of alloy sparks is determined. Based on this correlation equation, the content of alloying component is determined from the total number of alloy sparks of steel material.

By using the judgment device 14, the result of judgment of whether a steel material consists of a carbon steel or a low-alloy steel and the content of alloying component of steel material consisting of a low-alloy steel are displayed on a result displaying device 15 such as a monitor, or is stored in a storage device 16 such as a hard disk, memory, or the like.

Figure 8:
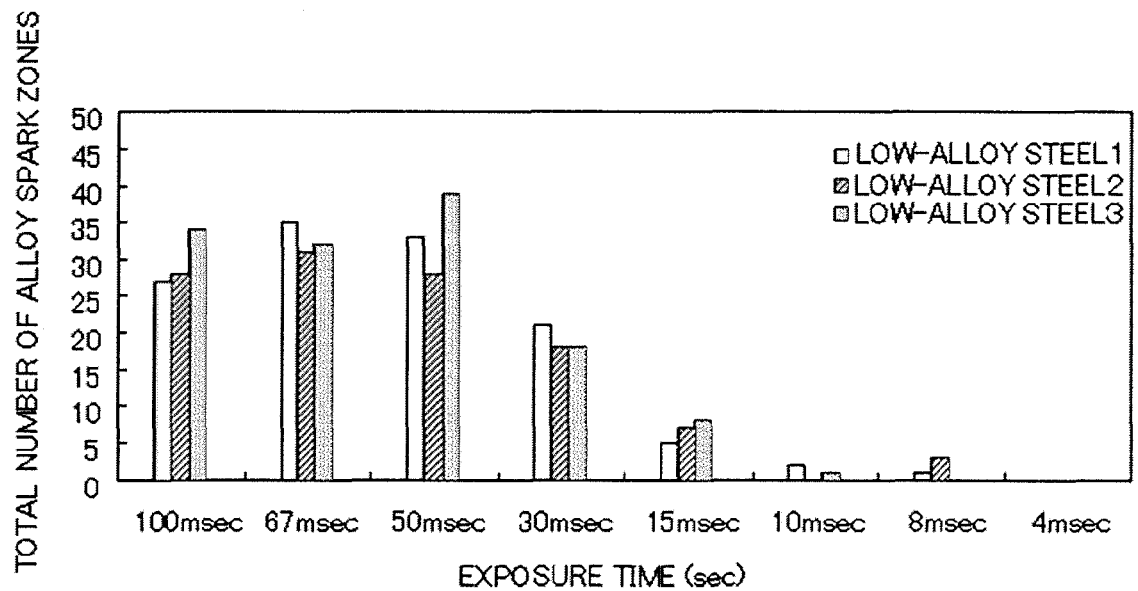
FIG. 8 is a graph showing the relationship between the exposure time of an image pickup device and the number of spark zones appearing in a picked-up image in the case where three steel materials each consisting of a low-alloy steel are ground with the circumferential speed of the grindstone of a grinder being set at 30 m/sec.

The preferable exposure time of the image pickup device 11 is in the range of 15 msec to 250 msec in the case where the circumferential speed of the grindstone is 30 m/msec. If the exposure time is shorter than the above-described range, the spark zone becomes small on the picked-up image 2. Therefore, as shown in FIG. 8, it is difficult to detect the alloy spark zone from the picked-up image 2. On the other hand, if the exposure time is longer than the above-described range, the spark zones overlap with each other, and each one of spark zones cannot be distinguished. Therefore, it is difficult to detect the alloy spark zone exactly from the picked-up image 2. In the above-described judgment in which sparks are observed visually by the inspector, it is conceivable that the inspector sights alloy sparks by means of the after-image effect. In order for the inspector to recognize alloy sparks visually and in order for the alloy sparks to be photographed on the picked-up image, the exposure time is preferably made equivalent to the time period for which the after-image effect is produced (50 to 250 msec).

Figure 9:
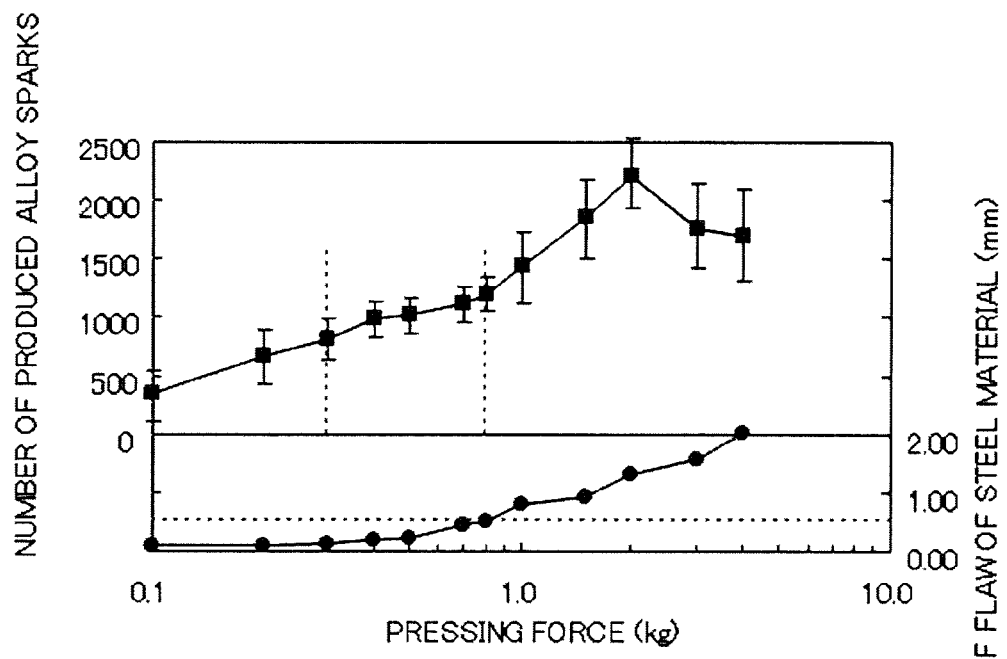
FIG. 9 is a graph showing the relationship between the pressing force of the peripheral face of the grindstone of a grinder against a steel material and the number of produced sparks and the depth of a flaw induced in the steel material.

As described above, in this embodiment, the force with which the peripheral face of the grindstone 171 is pressed against the steel material 18 is not lower than 2.94 N and not higher than 9.8 N. If the force with which the peripheral face of the grindstone 171 is pressed against the steel material 18 is made not lower than 2.94 N, as shown in FIG. 9, the number of produced alloy sparks is stabilized. Therefore, according to this embodiment, whether the steel material consists of a carbon steel or a low-alloy steel can be judged stably and accurately. If the pressing force is made not higher than 9.8 N, as shown in FIG. 9, the steel material 18 can be ground without the occurrence of deep flaws in the steel material 18. Therefore, according to this embodiment, the above-described judgment can be made stably and accurately without the occurrence of deep flaws in the steel material 18.

In the above description, only the spark zone falling under all of the first to third determination patterns is detected as an alloy spark zone. However, the spark zone falling under the first determination pattern, the spark zone falling under the first and second determination patterns, or the spark zone falling under the first and third determination patterns may be detected as an alloy spark zone.

The invention claimed is:

1. An apparatus for determining the kind of a steel material, comprising:
   an image pickup device for imaging a spark, which is produced when the steel material is ground, continuously a plurality of times;
   a detection device for detecting an alloy spark zone, which corresponds to an alloy spark produced by the grinding of an alloying component contained in the steel material, from each of picked-up images imaged by the image pickup device;
   a calculation device for calculating the total number of alloy spark zones by summing up the number of alloy spark zones of each picked-up image detected by the detection device for all of the picked-up images; and
   a judgment device for determining that the steel material consists of a low-alloy steel if the total number is not smaller than a first threshold value, and determining that the steel material consists of a carbon steel if the total number is smaller than the first threshold value, wherein the detection device performs:
   first processing in which a spark candidate pixel group consisting of pixels which are continuous with each other along a pixel line and have a density not lower than a second threshold value is detected for one pixel line constituting each of the picked-up images;
   second processing in which a highest density of pixels constituting the spark candidate pixel group is detected, and the pixels constituting each of a plurality of spark candidate pixel groups are binarized by a third threshold value which is lower than the highest density and larger than the second threshold value, whereby the pixels constituting a spark pixel group are detected from the pixels constituting each of the plurality of spark candidate pixel groups;
   third processing in which a binarized image representing the spark pixel group is prepared by executing the first processing and the second processing for all of the pixel lines constituting each of the picked-up images, and the spark pixel group continuous on the binarized image is recognized as a spark zone corresponding to a spark produced when the steel material is ground; and
   fourth processing in which the alloy spark zone is detected from the spark zone recognized by the third processing.

2. The apparatus for determining the kind of a steel material according to claim 1, wherein
   the fourth processing comprises:
   determination processing for determining whether or not the spark zone recognized by the third processing falls under a first determination pattern based on the ratio of the width of an end portion on the front side in the spark scatter direction to the width of an end portion on the rear side in the spark scatter direction in the spark zone recognized by the third processing; and
   detection processing for detecting the spark zone determined to fall under the first determination pattern by the determination processing as the alloy spark zone.

3. The apparatus for determining the kind of a steel material according to claim 2, wherein
   the determination processing determines whether or not the spark zone recognized by the third processing falls under the first determination pattern, and also determines whether or not the spark zone recognized by the third processing falls under a second determination pattern based on the relationship between the direction of the spark zone recognized by the third processing and the direction of another rear spark zone which is present at the rear in the scatter direction of the spark zone, and the length of the rear spark zone; and
   the detection processing detects the spark zone determined to fall under the first and second determination patterns by the determination processing as the alloy spark zone.

4. The apparatus for determining the kind of a steel material according to claim 3, wherein
   the determination processing determines whether or not the spark zone recognized by the third processing falls under the first and second determination patterns, and also determines whether or not the spark zone recognized by the third processing falls under a third determination pattern based on the distance between the spark zone recognized by the third processing and the rear spark zone; and
   the detection processing detects the spark zone determined to fall under all of the first to third determination patterns by the determination processing as the alloy spark zone.

5. The apparatus for determining the kind of a steel material according to claim 2, wherein
   the determination processing determines whether or not the spark zone recognized by the third processing falls under the first determination pattern, and also determines whether or not the spark zone recognized by the third processing falls under a third determination pattern based on the distance between the spark zone recognized by the third processing and another rear spark zone which is present at the rear in the scatter direction of the spark zone; and
   the detection processing detects the spark zone determined to fall under the first and third determination patterns by the determination processing as the alloy spark zone.

6. The apparatus for determining the kind of a steel material according to claim 1, wherein in the case where the steel material consists of a low-alloy steel, the judgment device determines the content of the alloying component in the steel material based on the total number.

7. A method for determining the kind of a steel material, comprising:
- an imaging step of imaging a spark, which is produced when the steel material is ground, continuously a plurality of times;
- a detecting step of detecting an alloy spark zone corresponding to an alloy spark, which is produced by the grinding of an alloying component contained in the steel material, from each of the picked-up images imaged in the imaging step;
- a calculating step of calculating the total number of alloy spark zones by summing up the number of alloy spark zones of each picked-up image detected in the detecting step for all of the picked-up images; and
- a judging step of determining that the steel material consists of a low-alloy steel if the total number is not smaller than a first threshold value, and determining that the steel material consists of a carbon steel if the total number is smaller than the first threshold value, wherein the detecting step includes:
- first processing in which a spark candidate pixel group consisting of pixels which are continuous with each other along a pixel line and have a density not lower than a second threshold value is detected for one pixel line constituting each of the picked-up images;
- second processing in which a highest density of pixels constituting the spark candidate pixel group is detected, and the pixels constituting each of a plurality of spark candidate pixel groups are binarized by a third threshold value which is lower than the highest density and larger than the second threshold value, whereby the pixels constituting a spark pixel group are detected from the pixels constituting each of the plurality of spark candidate pixel groups;
- third processing in which a binarized image representing the spark pixel group is prepared by executing the first processing and the second processing for all of the pixel lines constituting each of the picked-up images, and the spark pixel group continuous on the binarized image is recognized as a spark zone corresponding to a spark produced when the steel material is ground; and
- fourth processing in which the alloy spark zone is detected from the spark zone recognized by the third processing.

8. The method for determining the kind of a steel material according to claim 7, wherein in the imaging step, a spark produced when the steel material is ground by a grinding member pressed against the steel material with a force not lower than 2.94 N and not higher than 9.8 N is imaged.

* * * * *